US011708422B2

(12) United States Patent
Margulies et al.

(10) Patent No.: US 11,708,422 B2
(45) Date of Patent: Jul. 25, 2023

(54) MITIGATION OF LUNG INJURY

(71) Applicant: The Trustees Of The University Of Pennsylvania, Philadelphia, PA (US)

(72) Inventors: Susan S. Margulies, Villanova, PA (US); Nadir Yehya, Cherry Hill, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 320 days.

(21) Appl. No.: 16/885,545

(22) Filed: May 28, 2020

(65) Prior Publication Data
US 2020/0291132 A1  Sep. 17, 2020

Related U.S. Application Data

(62) Division of application No. 15/360,197, filed on Nov. 23, 2016, now abandoned.

(60) Provisional application No. 62/278,299, filed on Jan. 13, 2016.

(51) Int. Cl.
*C07K 16/32* (2006.01)
*A61K 31/428* (2006.01)
*A61K 39/00* (2006.01)

(52) U.S. Cl.
CPC ............ *C07K 16/32* (2013.01); *A61K 31/428* (2013.01); *A61K 2039/505* (2013.01); *C07K 2317/24* (2013.01); *C07K 2317/76* (2013.01)

(58) Field of Classification Search
CPC ............ A61K 31/428; A61K 2039/505; C07K 2317/76; C07K 2317/24; C07K 16/32
USPC ...................................................... 424/179.1
See application file for complete search history.

(56) References Cited

PUBLICATIONS

Bierman et al. (Translational Research, 2008, 152: 265-272).*
EGFR_HER1-MeSH-NCBI (Aug. 15, 2006, p. 1).*
Adam, L., et al., Heregulin regulates cytoskeletal reorganization and cell migration through the p21-activated kinase-1 via phosphatidylinositol-3 kinase. The Journal of biological chemistry, 1998. 273(43): p. 28238-46.
Ahmed, K.M., N. Cao, and J.J. Li, HER-2 and NF-kappaB as the targets for therapy-resistant breast cancer. Anticancer Res, 2006. 26(6B): p. 4235-43.
Bacallao, R., et al., ATP depletion: a novel method to study junctional properties in epithelial tissues. I. Rearrangement of the actin cytoskeleton. Journal of Cell Science, 1994. 107(Pt 12): p. 3301-13.
Baibazarova, E., et al., Influence of prenatal maternal stress, maternal plasma cortisol and cortisol in the amniotic fluid on birth outcomes and child temperament at 3 months. Psychoneuroendocrinology, 2013. 38(6): p. 907-15.
Baida, M.S. and K. Matter, Transmembrane proteins of tight junctions. Seminars in Cell & Developmental Biology, 2000. 11(4): p. 281-9.
Balestreire, E.M. and G. Apodaca, Apical epidermal growth factor receptor signaling: regulation of stretch-dependent exocytosis in bladder umbrella cells. Molecular biology of the cell, 2007. 18(4): p. 1312-23.
Basuroy, S., et al., Expression of kinase-inactive c-Src delays oxidative stress-induced disassembly and accelerates calcium-mediated reassembly of tight junctions in the Caco-2 cell monolayer. The Journal of biological chemistry, 2003. 278(14): p. 11916-24.
Basuroy, S., et al., MAPK interacts with occludin and mediates EGF-induced prevention of tight junction disruption by hydrogen peroxide. The Biochemical journal, 2006. 393(Pt 1): p. 69-77.
Bell, H.L. and M. Gooz, ADAM-17 is activated by the mitogenic protein kinase ERK in a model of kidney fibrosis. The American journal of the medical sciences, 2010. 339(2): p. 105-7.
Boitano, S., et al., Cell-cell interactions in regulating lung function. Am J Physiol Lung Cell Mol Physiol, 2004. 287(3): p. L455-9.
Borok, Z. and A.S. Verkman, Lung edema clearance: 20 years of progress: invited review: role of aquaporin water channels in fluid transport in lung and airways. J Appl Physiol, 2002. 93(6): p. 2199-206.
Brower, R.G. and G.D. Rubenfeld, Lung-protective ventilation strategies in acute lung injury. Critical Care Medicine, 2003. 31(4 Suppl): p. S312-6.
Brower, R.G., et al., Higher versus lower positive end-expiratory pressures in patients with the acute respiratory distress syndrome. N Engl J Med, 2004. 351(4): p. 327-36.

(Continued)

*Primary Examiner* — Yan Xiao
(74) *Attorney, Agent, or Firm* — BakerHostetler

(57) ABSTRACT

Inhibition of human epidermal growth factor receptor 2, human epidermal growth factor receptor 3, or of the heterodimerization of these proteins has presently been found to mitigate mechanically-induced lung injury or a lung-stretch injury. Provided are methods for treating a mechanically-induced lung injury or a lung-stretch injury, for increasing lung compliance, moderating alveolar epithelial permeability, or both in a subject having a mechanically-induced lung injury or a lung-stretch injury, for protecting a subject against a decrease in lung compliance, an increase in alveolar epithelial permeability, or both, as a result of a mechanically-induced lung injury or a lung-stretch injury, such methods involving the administration of an inhibitor of human epidermal growth factor receptor 2 (HER2) or human epidermal growth factor receptor 3 (HER3), or an inhibitor of the heterodimerization of HER2/HER3.

7 Claims, 3 Drawing Sheets

(56) References Cited

PUBLICATIONS

Brower, R.G., et al., Ventilation with lower tidal volumes as compared with traditional tidal volumes for acute lung injury and the acute respiratory distress syndrome. New England Journal of Medicine, 2000. 342(18): p. 1301-8.

Budinger, G.R., et al., Stretch-induced activation of AMP kinase in the lung requires dystroglycan. Am J Respir Cell Mol Biol, 2008. 39(6): p. 666-72.

Burdett, I.D., Aspects of the structure and assembly of desmosomes. Micron, 1998. 29(4): p. 309-28.

Cavanaugh, K.J. and S.S. Margulies, Measurement of stretch-induced loss of alveolar epithelial barrier integrity with a novel in vitro method. Am J Physiol Cell Physiol, 2002. 283(6): p. C1801-C1808.

Cavanaugh, K.J., J. Oswari, and S.S. Margulies, Role of stretch on tight junction structure in alveolar epithelial cells. American Journal of Respiratory Cell & Molecular Biology, 2001. 25(5): p. 584-91.

Cavanaugh, K.J., T.S. Cohen, and S.S. Margulies, Stretch increases alveolar epithelial permeability to uncharged micromolecules. Am J Physiol Cell Physiol, 2006. 290(4): p. C1179-88.

Chattopadhyay, R., et al., Vascular endothelial tight junctions and barrier function are disrupted by 15(S)-hydroxyeicosatetraenoic acid partly via protein kinase C epsilon-mediated zona occludens-1 phosphorylation at threonine 770/772. The Journal of biological chemistry, 2014. 289(6): p. 3148-63.

Chen, Y., et al., COOH terminus of occludin is required for tight junction barrier function in early Xenopus embryos. Journal of Cell Biology, 1997. 138(4): p. 891-9.

Chen, Y.T., et al., Cigarette smoke induces epidermal growth factor receptor-dependent redistribution of apical MUC1 and junctional beta-catenin in polarized human airway epithelial cells. The American journal of pathology, 2010. 177(3): p. 1255-64.

Chiumello, D., et al., Lung stress and strain during mechanical ventilation for acute respiratory distress syndrome. American Journal of Respiratory & Critical Care Medicine, 2008. 178(4): p. 346-55.

Cohen, T.S., et al., MAPK activation modulates permeability of isolated rat alveolar epithelial cell monolayers following cyclic stretch. PloS one, 2010. 5(4): p. e10385.

Cohen, T.S., et al., Sepsis enhances epithelial permeability with stretch in an actin dependent manner. PloS one, 2012. 7(6): p. e38748.

Cohen, T.S., G. Gray Lawrence, and S.S. Margulies, Cultured alveolar epithelial cells from septic rats mimic in vivo septic lung. PloS one, 2010. 5(6): p. e11322.

Correa-Meyer, E., et al., Cyclic stretch activates ERK1/2 via G proteins and EGFR in alveolar epithelial cells. Am J Physiol Lung Cell Mol Physiol, 2002. 282(5): p. L883-91.

Davidovich, N., et al., Cyclic stretch-induced oxidative stress increases pulmonary alveolar epithelial permeability. Am J Respir Cell Mol Biol, 2013. 49(1): p. 156-64.

Davidovich, N., J. Huang, and S.S. Margulies, Reproducible uniform equibiaxial stretch of precision-cut lung slices. Am J Physiol Lung Cell Mol Physiol, 2013. 304(4): p. L210-20.

Denker, B.M. and S.K. Nigam, Molecular structure and assembly of the tight junction. American Journal of Physiology, 1998. 274(1 Pt 2): p. F1-9.

Dipaolo, B.C., et al., Rac1 pathway mediates stretch response in pulmonary alveolar epithelial cells. Am J Physiol Lung Cell Mol Physiol, 2013. 305(2): p. L141-53.

DiPaolo, B.C., et al., Stretch magnitude and frequency-dependent actin cytoskeleton remodeling in alveolar epithelia. Am J Physiol Cell Physiol, 2010. 299(2): p. C345-53.

Dolinay, T., et al., Gene expression profiling of target genes in ventilator-induced lung injury. Physiological genomics, 2006. 26(1): p. 68-75.

Dos Santos, C.C. and A.S. Slutsky, Invited review: mechanisms of ventilator-induced lung injury: a perspective. [see comments]. Journal of Applied Physiology, 2000. 89(4): p. 1645-55.

Dreyfuss et al., "High inflation pressure pulmonary edema. Respective effects of high airway pressure, high tidal volume, and positive end-expiratory pressure", Am Rev Respir Dis, 1988. 137(5): p. 1159-64.

Dreyfuss, D. and G. Saumon, Barotrauma is volutrauma, but which volume is the one responsible? Intensive Care Medicine, 1992. 18(3): p. 139-41.

Dreyfuss, D. and G. Saumon, Role of tidal volume, FRC, and end-inspiratory volume in the development of pulmonary edema following mechanical ventilation. American Review of Respiratory Disease, 1993. 148(5): p. 1194-203.

Dreyfuss, D. and G. Saumon, Ventilator-induced lung injury: lessons from experimental studies. American Journal of Respiratory & Critical Care Medicine, 1998. 157(1): p. 294-323.

Dubrovskyi, O., A.A. Birukova, and K.G. Birukov, Measurement of local permeability at subcellular level in cell models of agonist- and ventilator-induced lung injury. Lab Invest, 2013. 93(2): p. 254-63.

Dudek, S.M. and J.G. Garcia, Cytoskeletal regulation of pulmonary vascular permeability. Journal of Applied Physiology, 2001. 91(4): p. 1487-500.

Dunn, C.A. and P.D. Lampe, Injury-triggered Akt phosphorylation of Cx43: a ZO-1-driven molecular switch that regulates gap junction size. Journal of cell science, 2014. 127(Pt2): p. 455-64.

Egan, E.A., Lung inflation, lung solute permeability, and alveolar edema. Journal of Applied Physiology: Respiratory, Environmental & Exercise Physiology, 1982. 53(1): p. 121-5.

Elias, B.C., et al., Phosphorylation of Tyr-398 and Tyr-402 in occludin prevents its interaction with ZO-1 and destabilizes its assembly at the tight junctions. The Journal of biological chemistry, 2009. 284(3): p. 1559-69.

Evans, W.H. and P.E. Martin, Lighting up gap junction channels in a flash. Bioessays, 2002. 24(10): p. 876-80.

Fanelli, V., et al., Pulmonary-derived phosphoinositide 3-kinase gamma (PI3Kgamma) contributes to ventilator-induced lung injury and edema. Intensive Care Med, 2010. 36(11): p. 1935-45.

Fasanaro, P., et al., microRNA: emerging therapeutic targets in acute ischemic diseases. Pharmacol Ther, 2010. 125(1): p. 92-104.

Finigan et al., JBC Papers in Published on Jan. 19, 2011 as Manuscript M110.208041.

Finigan, J., et al., Neuregulin-1 Human Epidermal Receptor-2 Signalling is a Central Regulator of Pulmonary Epithelial Permeability and Acute Lung Injury. J Biol Chem, 2011.

Finigan, J.H., et al., Bronchoalveolar lavage neuregulin-1 is elevated in acute lung injury and correlates with inflammation. Eur Respir J, 2013. 41 (2): p. 396-401.

Finigan, J.H., G.P. Downey, and J.A. Kern, Human epidermal growth factor receptor signaling in acute lung injury. American journal of respiratory cell and molecular biology, 2012. 47(4): p. 395-404.

Fleck, D., et al., Dual cleavage of neuregulin 1 type III by BACE1 and ADAM17 liberates its EGF-like domain and allows paracrine signaling. The Journal of neuroscience : the official journal of the Society for Neuroscience, 2013. 33(18): p. 7856-69.

Fu, Z., et al., High lung volume increases stress failure in pulmonary capillaries. Journal of Applied Physiology, 1992. 73(1): p. 123-33.

Gooz, P., et al., A disintegrin and metalloenzyme (ADAM) 17 activation is regulated by alpha5beta1 integrin in kidney mesangial cells. PloS one, 2012. 7(3): p. e33350.

Gorin, A.B. and P.A. Stewart, Differential permeability of endothelial and epithelial barriers to albumin flux. Journal of Applied Physiology: Respiratory, Environmental & Exercise Physiology, 1979. 47(6): p. 1315-24.

Haake, R., et al., Barotrauma. Pathophysiology, risk factors, and prevention. Chest, 1987. 91(4): p. 608-13.

Iivanainen, E., et al., Intra- and extracellular signaling by endothelial neuregulin-1. Experimental cell research, 2007. 313(13): p. 2896-909.

Johnson, E.R. and M.A. Matthay, Acute lung injury: epidemiology, pathogenesis, and treatment. Journal of aerosol medicine and pulmonary drug delivery, 2010. 23(4): p. 243-52.

(56) References Cited

PUBLICATIONS

Kim, K.J. and E.D. Crandall, Effects of lung inflation on alveolar epithelial solute and water transport properties. Journal of Applied Physiology: Respiratory, Environmental & Exercise Physiology, 1982. 52(6): p. 1498-505.
Kwak, E., The role of irreversible HER family inhibition in the treatment of patients with non-small cell lung cancer. Oncologist, 2011. 16(11): p. 1498-507.
La Marca, R., et al., TACE (ADAM17) inhibits Schwann cell myelination. Nature neuroscience, 2011. 14(7): p. 857-65.
Lecuona, E., et al., Ventilator-associated lung injury decreases lung ability to clear edema in rats. American Journal of Respiratory & Critical Care Medicine, 1999. 159(2): p. 603-9.
Li, L.F., et al., Lumican regulates ventilation-induced epithelial-mesenchymal transition through extracelluar signal-regulated kinase pathway. Chest, 2013. 143(5): p. 1252-60.
Li, Q., et al., Interferon-gamma and tumor necrosis factor-alpha disrupt epithelial barrier function by altering lipid composition in membrane microdomains of tight junction Clin Immunol, 2008. 126(1): p. 67-80.
Lubman, R.L., K.J. Kim, and E.D. Crandall, Alveolar Epithelial Barrier Properties, in The Lung: Scientific Foundations, R.G. Crystal and J.B. West, Editors. 1997, Lippincott-Raven: Philadelphia. p. 585-602.
Luo, Z., et al., Comparison of inhibitors of superoxide generation in vascular smooth muscle cells. British journal of pharmacology, 2009. 157(6): p. 935-43.
Maresch, J., et al., Her-2/neu gene amplification and overexpression in stomach and esophageal adenocarcinoma: from pathology to treatment. Crit Rev Oncol Hematol, 2012. 82(3): p. 310-22.
Matthay, M.A., et al., Ventilator-induced lung injury: in vivo and in vitro mechanisms. Am J Physiol Lung Cell Mol Physiol, 2002. 283(4): p. L678-82.
Mazzon, E. and S. Cuzzocrea, Role of TNF-alpha in lung tight junction alteration in mouse model of acute lung inflammation. Respir Res, 2007. 8: p. 75.
Mitic, L.L. and J.M. Anderson, Molecular architecture of tight junctions. Annual Review of Physiology, 1998. 60: p. 121-42.
Murakami, T., E.A. Felinski, and D.A. Antonetti, Occludin phosphorylation and ubiquitination regulate tight junction trafficking and vascular endothelial growth factor-induced permeability. J Biol Chem, 2009. 284(31): p. 21036-46.
Muscedere, J.G., et al., Tidal ventilation at low airway pressures can augment lung injury. Am J Respir Crit Care Med, 1994. 149(5): p. 1327-34.
Muthuswamy, S.K., et al., ErbB2, but not ErbB1, reinitiates proliferation and induces luminal repopulation in epithelial acini. Nat Cell Biol, 2001. 3(9): p. 785-92.
National Heart, L., et al., Comparison of two fluid-management strategies in acute lung injury. N Engl J Med, 2006. 354(24): p. 2564-75.
Nguyen, H.T., et al., Heparin-binding EGF-like growth factor is up-regulated in the obstructed kidney in a cell- and region-specific manner and acts to inhibit apoptosis. The American journal of pathology, 2000. 156(3): p. 889-98.
Nobes, C.D. and A. Hall, Rho, rac and cdc42 GTPases: regulators of actin structures, cell adhesion and motility. Biochem Soc Trans, 1995. 23(3): p. 456-9.
Otulakowski, G., et al., Hypercapnia attenuates ventilator-induced lung injury via a disintegrin and metalloprotease-17. The Journal of physiology, 2014. 592(Pt 20): p. 4507-21.
Park, S., et al., ERK/MAPK pathways play critical roles in EGFR ligands-induced MMP1 expression. Biochemical and biophysical research communications, 2011.
Parker, J.C., L.A. Hernandez, and K.J. Peevy, Mechanisms of ventilator-induced lung injury. Critical Care Medicine, 1993. 21(1): p. 131-43.
Patel, A.S., et al., Paracrine stimulation of surfactant secretion by extracellular ATP in response to mechanical deformation. Am J Physiol Lung Cell Mol Physiol, 2005.
Perrella, M.A., et al., Regulation of heparin-binding epidermal growth factor-like growth factor mRNA levels by hypertrophic stimuli in neonatal and adult rat cardiac myocytes. The Journal of biological chemistry, 1994. 269(43): p. 27045-50.
Perussi, L.R., et al., Effects of the Er,Cr:YSGG laser on bone and soft tissue in a rat model. Lasers in medical science, 2012. 27(1): p. 95-102.
Potard, U.S., J.P. Butler, and N. Wang, Cytoskeletal mechanics in confluent epithelial cells probed through integrins and E-cadherins. American Journal of Physiology, 1997. 272(5 Pt 1): p. C1654-63. Abstract.
Qureshi, S.T., et al., Inducible activation of TLR4 confers resistance to hyperoxia-induced pulmonary apoptosis. J Immunol, 2006. 176(8): p. 4950-8.
Ragaller et al., J. Emerg. Trauma Shock, Jan.-Mar. 2010, 3(1), 43-51.
Rao, R., Occludin phosphorylation in regulation of epithelial tight junctions. Annals of the New York Academy of Sciences, 2009. 1165: p. 62-8.
Rezaee, F. and S.N. Georas, Breaking barriers. New insights into airway epithelial barrier function in health and disease. American journal of respiratory cell and molecular biology, 2014. 50(5): p. 857-69.
Ricard, J.D., D. Dreyfuss, and G. Saumon, Ventilator-induced lung injury. Eur Respir J Suppl, 2003. 42: p. 2s-9s.
Rodgers, L.S., et al., Epithelial barrier assembly requires coordinated activity of multiple domains of the tight junction protein ZO-1. Journal of cell science, 2013. 126(Pt 7): p. 1565-75.
Rowinsky, E.K., Signal events: Cell signal transduction and its inhibition in cancer. Oncologist, 2003. 8 Suppl 3: p. 5-17.
Sahin, U., et al., Distinct roles for ADAM10 and ADAM17 in ectodomain shedding of six EGFR ligands. The Journal of cell biology, 2004. 164(5): p. 769-79.
Saitou, M., et al., Mammalian occludin in epithelial cells: its expression and subcellular distribution. European Journal of Cell Biology, 1997. 73(3): p. 222-31.
Samak, G., et al., Cyclic stretch disrupts apical junctional complexes in Caco-2 cell monolayers by a JNK-2-, c-Src-, and MLCK-dependent mechanism. American journal of physiology. Gastrointestinal and liver physiology, 2014. 306(11): p. G947-58.
Schneeberger, E.E. and R.D. Lynch, Ultrastructure of the distal pulmonary epithelium, in Fluid and Solute Transport in the Airspaces of the Lungs, R.M. Effros and H.K. Chang, Editors. 1994, Marcel Dekker: New York. p. 1-25.
Sergina, N.V. and M.M. Moasser, The HER family and cancer: emerging molecular mechanisms and therapeutic targets. Trends in molecular medicine, 2007. 13(12): p. 527-34.
Sheth, P., et al., Role of phosphatidylinositol 3-kinase in oxidative stress-induced disruption of tight junctions. The Journal of biological chemistry, 2003. 278(49): p. 49239-45.
Singleton, K.D., V.E. Beckey, and P.E. Wischmeyer, Glutamine Prevents Activation Of NFkappaB And Stress Kinase Pathways, Attenuates Inflammatory Cytokine Release, and Prevents Acute Respiratory Distress Syndrome (ARDS) Following Sepsis. Shock, 2005. 24(6): p. 583-9.
Slutsky, A.S. and V.M. Ranieri, Ventilator-induced lung injury. The New England journal of medicine, 2013. 369(22): p. 2126-36.
Stevenson, B.R., et al., Phosphorylation of the tight-junction protein ZO-1 in two strains of Madin-Darby canine kidney cells which differ in transepithelial resistance. Biochemical Journal, 1989. 263(2): p. 597-9.
Subramanian, A., et al., Gene set enrichment analysis: a knowledge-based approach for interpreting genome-wide expression profiles. Proc Natl Acad Sci U S A, 2005. 102(43): p. 15545-50.
Suzuki, T., et al., PKC eta regulates occludin phosphorylation and epithelial tight junction integrity. Proceedings of the National Academy of Sciences of the United States of America, 2009. 106(1): p. 61-6.
Tepass, U., Adherens junctions: new insight into assembly, modulation and function. Bioessays, 2002. 24(8): p. 690-5.
Tice, L.W., R.L. Carter, and M.C. Cahill, Tracer and freeze fracture observations on developing tight junctions in fetal rat thyroid. Tissue Cell, 1977. 9(3): p. 395-417.

(56) References Cited

PUBLICATIONS

Trinh, N.T., et al., Involvement of KATP and KvLQT1 K+ channels in EGF-stimulated alveolar epithelial cell repair processes. American journal of physiology. Lung cellular and molecular physiology, 2007. 293(4): p. L870-82.

Tschumperlin, D.J. and S.S. Margulies, Equibiaxial deformation-induced injury of alveolar epithelial cells in vitro. American Journal of Physiology, 1998. 275(6 Pt 1): p. L1173-83.

Tschumperlin, D.J., EGFR autocrine signaling in a compliant interstitial space: mechanotransduction from the outside in. Cell Cycle, 2004. 3(8): p. 996-7.

Tschumperlin, D.J., et al., Mechanotransduction through growth-factor shedding into the extracellular space. Nature, 2004. 429(6987): p. 83-6.

Tschumperlin, D.J., J. Oswari, and S.S. Margulies, Deformation-induced injury of alveolar epithelial cells. Effect of frequency, duration, and amplitude. Am J Respir Crit Care Med, 2000. 162(2 Pt 1): p. 357-62.

Tsujioka, H., et al., Emerging strategies for ErbB ligand-based targeted therapy for cancer. Anticancer Res, 2010. 30(8): p. 3107-12.

Tsukamoto, T. and S.K. Nigam, Tight junction proteins form large complexes and associate with the cytoskeleton in an ATP depletion model for reversible junction assembly. Journal of Biological Chemistry, 1997. 272(26): p. 16133-9.

Tsuno, K., et al., Histopathologic pulmonary changes from mechanical ventilation at high peak airway pressures. American Review of Respiratory Disease, 1991. 143(5 Pt 1): p. 1115-20.

Van der Horst, E.H., et al., Anti-HER-3 MAbs inhibit HER-3-mediated signaling in breast cancer cell lines resistant to anti-HER-2 antibodies. International journal of cancer. Journal international du cancer, 2005. 115(4): p. 519-27.

Walker, D.C., et al., Assessment of tight junctions between pulmonary epithelial and endothelial cells. Journal of Applied Physiology, 1988. 64(6): p. 2348-56.

Wang, F., et al., Heterogeneity of claudin expression by alveolar epithelial cells. Am J Respir Cell Mol Biol, 2003. 29(1): p. 62-70.

Wang, S.E., et al., HER2/Neu (ErbB2) signaling to Rac1-Pak1 is temporally and spatially modulated by transforming growth factor beta. Cancer research, 2006. 66(19): p. 9591-600.

Wang, Y., et al., Mechanical stretch promotes fetal type II epithelial cell differentiation via shedding of HB-EGF and TGF-alpha. The Journal of physiology, 2009. 587(Pt 8): p. 1739-53.

Ware, L.B. and M.A. Matthay, The acute respiratory distress syndrome. New England Journal of Medicine, 2000. 342(18): p. 1334-49.

Waters, C.M., et al., Mechanical stretching of alveolar epithelial cells increases Na(+)-K(+)-ATPase activity. Journal of Applied Physiology, 1999. 87(2): p. 715-21.

Wirtz, H.R. and L.G. Dobbs, Calcium mobilization and exocytosis after one mechanical stretch of lung epithelial cells. Science, 1990. 250(4985): p. 1266-9.

Wray, C., et al., Claudin-4 augments alveolar epithelial barrier function and is induced in acute lung injury. American journal of physiology. Lung cellular and molecular physiology, 2009. 297(2): p. L219-27.

Yehya, N., et al., MicroRNA modulate alveolar epithelial response to cyclic stretch. BMC Genomics, 2012. 13: p. 154.

Yerrapureddy, A., J. Tobias, and S.S. Margulies, Cyclic stretch magnitude and duration affect rat alveolar epithelial gene expression. Cell Physiol Biochem, 2010. 25(1): p. 113-22.

Zhang, Y., et al., HER/ErbB receptor interactions and signaling patterns in human mammary epithelial cells. BMC cell biology, 2009. 10: p. 78.

\* cited by examiner

MITIGATION OF LUNG INJURY

CROSS-REFERENCE TO RELATED APPLICATIONS

This application is a divisional of U.S. Ser. No. 15/360,197, filed on Nov. 23, 2016, which claims the benefit of priority to U.S. Provisional Application No. 62/278,299, filed Jan. 13, 2016, the entire contents of both of which are incorporated herein by reference.

GOVERNMENT RIGHTS

This invention was made with government support under Grant Number R01HL57204 awarded by the National Institutes of Health—National Heart, Lung and Blood Institute. The government has certain rights in the invention.

TECHNICAL FIELD

The present disclosure pertains to treatments for lung injury, such as lung injury that is mechanically induced or caused by lung stretch.

BACKGROUND

Mechanical ventilator-induced lung injury (VILI) occurs in 5% to 15% of all patients who require mechanical ventilation, or 200,000 annually in the United States, with a mortality rate of 34-60% in ventilated patients with adult respiratory distress syndrome (ARDS). VILI is characterized by alveolar cell dysfunction and profound changes in barrier permeability. Human and animal studies have demonstrated that VILI is associated with mechanical ventilation with high regional lung volumes, and may also be related to reopening of collapsed lung regions. Current management recommendations to limit worsening lung injury in patients with ARDS include use of low tidal volumes and conservative fluid protocols.

Overall, there is a paucity of options available for reducing the morbidity and mortality during ventilation, especially when small tidal volumes fail to achieve sufficient gas exchange. Furthermore, heterogeneity of ARDS lung contributes to a non-homogenous distribution of delivered volumes, thereby contributing to worsening VILI by over-distending more compliant lung regions, even when low tidal volumes are employed. A long-standing need exists to improve outcomes for all mechanically ventilated patients.

In VILI, gas exchange is compromised by the formation or worsening of edema in the alveolar airspaces, which decreases lung diffusivity and compliance. Although the endothelial barrier properties may be disrupted in VILI resulting in interstitial edema, the alveolar epithelium provides nearly all of the passive resistance to protein passage and over 90% of the resistance to the transport of nonpolar and charged solutes. Damage to the epithelium increases solute diffusion into the alveolar airspace, and water follows passively into the airspace along the osmotic gradient, causing the existence or worsening of pulmonary edema as seen in VILI, even with normal vascular function. The tight junction (TJ) and its component proteins of claudins (4, 5, 7, and 18) and occludin, as well as the zonula ocludens (ZO-1), which links the TJ to the cytoskeleton, are the primary regulators of paracellular resistance and charge selectivity in the alveolar epithelium. Previous studies investigated stretch magnitude-dependent changes in TJ protein and actin and barrier dysfunction. The mechanisms linking cell or tissue deformation with impaired epithelial barrier function and TJ disruption remain unknown. A need exists for the identification of injury intervention strategies that preserve barrier properties during mechanical ventilation.

SUMMARY

Provided herein are methods for treating a mechanically-induced lung injury or a lung-stretch injury in a subject comprising administering to the subject an inhibitor of human epidermal growth factor receptor 2 (HER2) or human epidermal growth factor receptor 3 (HER3), or an inhibitor of the heterodimerization of HER2/HER3.

Also disclosed are methods for increasing lung compliance, moderating alveolar epithelial permeability, or both in a subject having a mechanically-induced lung injury or a lung-stretch injury comprising administering to the subject an inhibitor of human epidermal growth factor receptor 2 (HER2) or human epidermal growth factor receptor 3 (HER3), or an inhibitor of the heterodimerization of HER2/HER3, thereby increasing lung compliance, moderating alveolar epithelial permeability, or both in the subject.

The present disclosure also pertains to methods for protecting a subject against a decrease in lung compliance, an increase in alveolar epithelial permeability, or both, as a result of a mechanically-induced lung injury or a lung-stretch injury comprising administering to the subject an inhibitor of human epidermal growth factor receptor 2 (HER2) or human epidermal growth factor receptor 3 (HER3), or an inhibitor of the heterodimerization of HER2/HER3, thereby protecting the subject against a decrease in lung compliance, an increase in alveolar epithelial permeability, or both.

Also provided are methods comprising administering an inhibitor of human epidermal growth factor receptor 2 (HER2) or human epidermal growth factor receptor 3 (HER3), or an inhibitor of the heterodimerization of HER2/HER3 to a subject that is undergoing or is to undergo mechanical ventilation.

DETAILED DESCRIPTION OF ILLUSTRATIVE EMBODIMENTS

Figure 1:
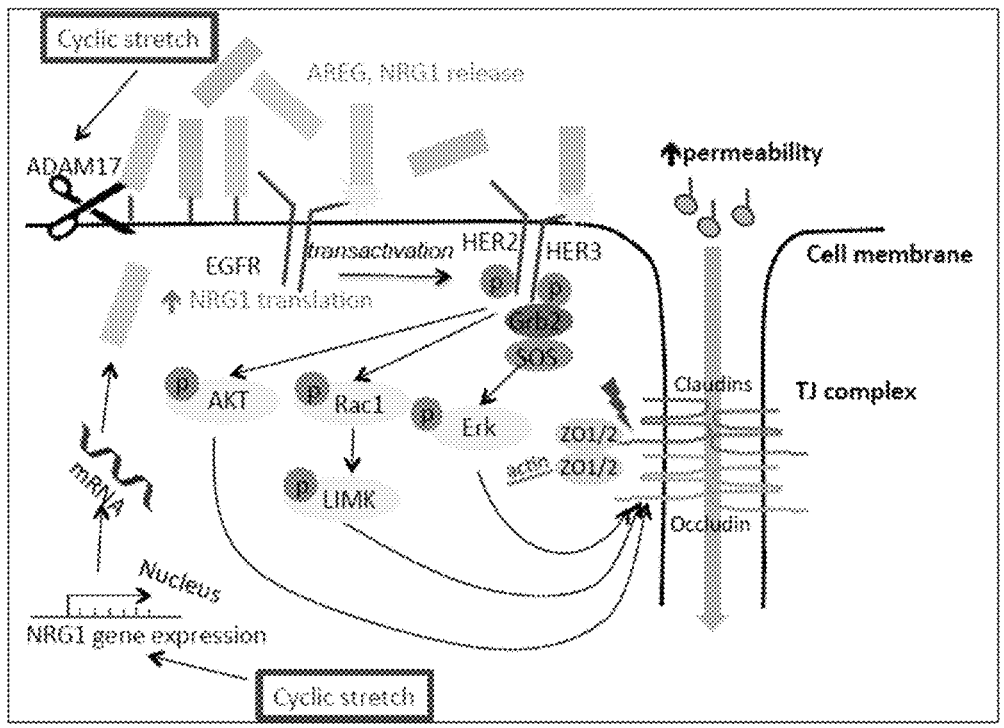
FIG. 1 depicts the pathway by which cyclic stretch activates HER2/HER3 heterodimerzation via cleavage of Neuregulinl (NRG1) in alveolar epithelial Type I cells.
Figure 2:
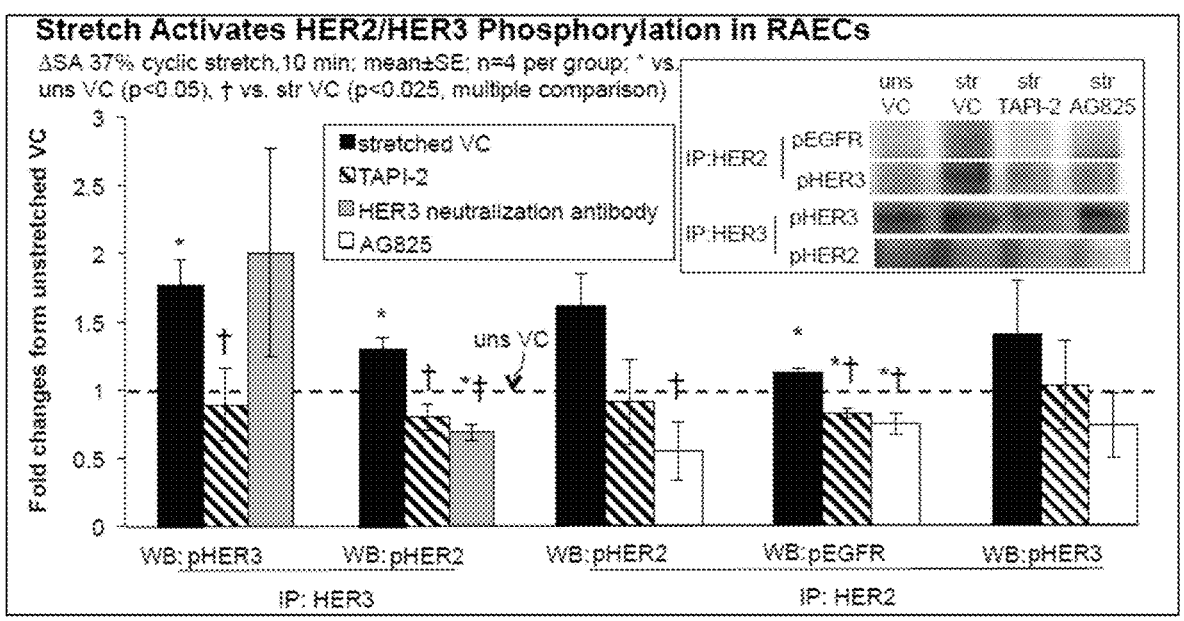
FIG. 2 illustrates the finding that stretch-induced release of NRG1 increases phosphorylation of HER2 and HER3, and enhances formation of HER2/HER3 heterodimers, and that inhibiting NRG1 cleavage decreases HER2 and HER3 phosphorylation and HER2 and HER3.
Figure 3:
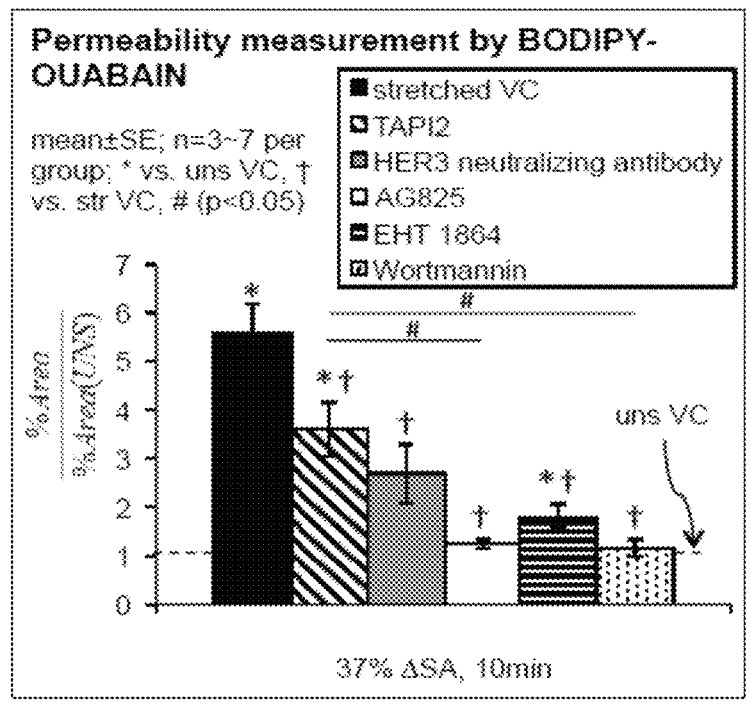
FIG. 3 shows that HER2/HER3 heterodimerzation and activation mediates epithelial permeability during stretch, as HER2 or HER3 inhibition results in moderation of permeability during stretch.
Figure 4:
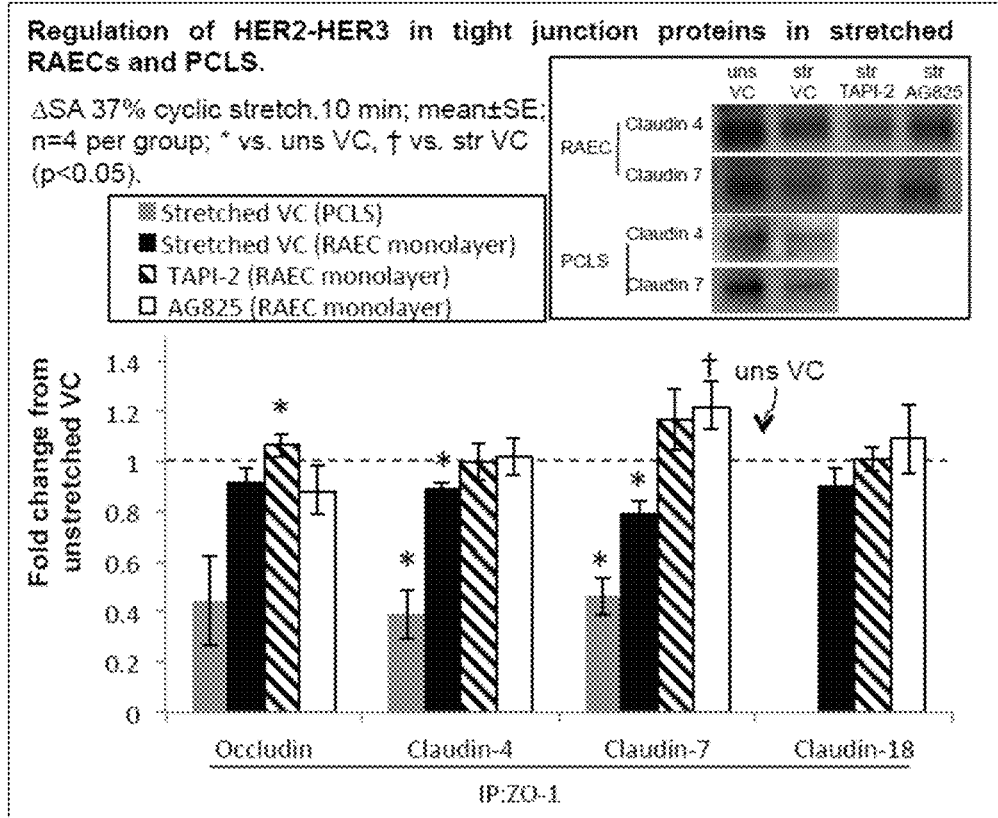
FIG. 4 shows that HER2/HER3 heterodimerzation and activation mediates tight junction dissociation during stretch, as inhibition of NRG1 cleavage (using TAPI-2) or of HER2 activation (using AG825) reduces stretch-induced tight junction dissociation.

The present invention may be understood more readily by reference to the following detailed description taken in connection with the accompanying figures and examples, which form a part this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

The entire disclosures of each patent, patent application, and publication cited or described in this document are hereby incorporated herein by reference.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "an inhibitor" is a reference to one or more of such inhibitors and equivalents thereof known to those skilled in the art, and so forth. Furthermore, when indicating that a certain element "may be" X, Y, or Z, it is not intended by such usage to exclude in all instances other choices for the element.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded; thus, a recitation of "1 to 5" may support "1 and 3-5, but not 2", or simply "wherein 2 is not included."

As used herein, the terms "treatment" or "therapy" (as well as different word forms thereof) includes preventative (e.g., prophylactic), curative, or palliative treatment. Such preventative, curative, or palliative treatment may be full or partial. For example, complete elimination of unwanted symptoms, or partial elimination of one or more unwanted symptoms would represent "treatment" as contemplated herein.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired response in the individual, but also with factors such as the disease state or severity of the condition to be alleviated, hormone levels, age, sex, weight of the individual, the state of being of the patient, and the severity of the condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects. As an example, the compounds useful in the methods of the present invention are administered at a dosage and for a time such that the level of activation and adhesion activity of platelets is reduced as compared to the level of activity before the start of treatment.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Provided herein are methods for treating a mechanically-induced lung injury or a lung-stretch injury, for increasing lung compliance, moderating alveolar epithelial permeability, or both in a subject having a mechanically-induced lung injury or a lung-stretch injury, for protecting a subject against a decrease in lung compliance, an increase in alveolar epithelial permeability, or both, as a result of a mechanically-induced lung injury or a lung-stretch injury, such methods involving the administration of an inhibitor of human epidermal growth factor receptor 2 (HER2) or human epidermal growth factor receptor 3 (HER3), or an inhibitor of the heterodimerization of HER2/HER3. Also disclosed are methods that comprise administering an inhibitor of human epidermal growth factor receptor 2 (HER2) or human epidermal growth factor receptor 3 (HER3), or an inhibitor of the heterodimerization of HER2/HER3 to a subject that is undergoing or is to undergo mechanical ventilation.

Mechanical ventilation helps mitigate live-threatening hypoxia and hypercapnia, but can damage a subject's lungs due to overinflation, barotrauma, and cyclic closing and reopening of the lung alveoli, which can trigger further systemic inflammatory reactions and multiple organ dysfunction and failure. At the time of the present disclosure, there are no specific therapies for mechanically-induced lung injury or a lung-stretch injury, and a need exists for adjunctive strategies that modulate or protect against the deleterious effects of mechanical ventilation.

It has presently been found that during mechanically-induced traumatic lung injury or tissue deformation, such as during mechanical ventilation, the human epidermal growth factor receptor (HER) family of genes is upregulated, and neuregulin (NRG1) is cleaved upon stretch induction. This released NRG1 binds HER3 and inhibits NRG/HER receptor binding, activating downstream signaling cascades, including tight junction protein dissociation and paracellular permeability. Although there has been some investigation into the causal link between NRG1 and acute lung injury (such as acute inflammatory lung injury and acute respiratory distress syndrome), the relevance of HER activation signaling has not been determined with respect to other models of lung injury, such as lung strategy or ventilator-associated lung injury. It has presently been discovered that inhibition of human epidermal growth factor receptor 2 (HER2), of human epidermal growth factor receptor 3 (HER3), or of the heterodimerization of HER2/HER3 preserves barrier properties and lung compliance, even during prolonged ventilation with large inspired volumes. The methods disclosed herein can therefore be used to treat or protect against mechanically induced lung injury, which occurs in 5-15% of patients requiring mechanical ventilation, with a mortality rate of 34-60%, and stretch injury.

Accordingly, provided herein are methods for treating a mechanically-induced lung injury or a lung-stretch injury in a subject comprising administering to the subject an inhibitor of human epidermal growth factor receptor 2 (HER2) or human epidermal growth factor receptor 3 (HER3), or an inhibitor of the heterodimerization of HER2/HER3. Mechanically-induced lung injury is an injury resulting, for example, from any form of mechanically assisted breathing, such as from positive pressure devices or negative pressure devices. Such injuries typically result from one or more of overinflation, barotrauma, and cyclic closing and reopening of the lung alveoli. Lung stretch injuries can also result from lung overinflation, barotrauma, and cyclic closing and reopening of the lung alveoli, but need not necessarily arise from mechanical ventilation. In preferred embodiments, the subject has a lung injury that is directly induced by mechanical ventilation, such as classical Ventilator Induced Lung Injury (VILI).

Any inhibitor of HER2, HER3, or of the heterodimerization of HER2/HER3 may be used in accordance with the present methods. Numerous inhibitors of one or more of these types have been developed pursuant to treatment for unrelated conditions, such as breast or colon cancers. Examples of HER2 inhibitors include AG825 (also known as Tyrphostin AG 825, and having the chemical formula name (E)-3-[3-[2-Benzothiazolythio)methyl]-4-hydroxy-5-methoxyphenyl]-2-cyano-2-propenamide), trastuzumab (sold as Herceptin® by Genentech, San Francisco, Calif.), pertuzumab, lapatinib, and AZD8931. Examples of HER3 inhibitors include AZD8931 and U3-1287 (AMG 888). Examples of inhibitors of the heterodimerization of HER2/HER3 include HER2Mab and LJM716. Inhibitors of any of the preceding types may be small molecules, antibodies, or may take any other form that provides the desired function. Other examples of inhibitors of members of the human epidermal growth factor receptor (HER) family are shown below in Table 1, which is not exhaustive.

TABLE 1

| Drug | Type | Target(s) | Sponsor |
|---|---|---|---|
| MM-121 (SAR256212) | Humanized mAb | HER3 | Merrimack |
| MM-111 | Bispecific antibody | HER2-HER3 | Merrimack |
| MEHD7945A | mAb | HER1, HER3 | Genentech |
| MP-470 (Amuvatinib) | Pan inhibitor | HER1/2/3 | Astex Pharmaceuticals |

In certain instances, an inhibitor of one of HER2, HER3, or of the heterodimerization of HER2/HER3 may also function as an inhibitor of another of HER2, HER3, or of the heterodimerization of HER2/HER3. For example, MP-470, shown in Table 1, targets both HER2 and HER3. It could also be said that a compound that inhibits HER2, such as AG825, also inherently inhibits HER2/HER3 heterodimerization via disruption of HER2 activity. Accordingly, recitation of "an inhibitor of HER2" is not meant to exclude substances that can inhibit HER3 and/or the heterodimerization of HER2/HER3, while also being able to inhibit HER2. Likewise, recitation of "an inhibitor of HER3" is not meant to exclude substances that can inhibit HER2 and/or the heterodimerization of HER2/HER3, while also being able to inhibit HER3. In the same way, recitation of "an inhibitor of the heterodimerization of HER2/HER3" is not meant to exclude substances that can inhibit HER2 and/or HER3, while also being able to inhibit the heterodimerization of HER2/HER3.

In accordance with the present methods, the inhibitor of HER2, HER3, or of the heterodimerization of HER2/HER3 are administered in a therapeutically effective amount. As used herein, the phrase "therapeutically effective amount" refers to the amount of active compound that elicits the biological or medicinal response that is being sought in a tissue, system, animal, individual or human by a researcher, veterinarian, medical doctor or other clinician, which includes one or more of the following:

(1) at least partially preventing the disease or condition or a symptom thereof; for example, preventing a disease, condition or disorder in an individual who may be predisposed to the disease, condition or disorder but does not yet experience or display the pathology or symptomatology of the disease;

(2) inhibiting the disease or condition; for example, inhibiting a disease, condition or disorder in an individual who is experiencing or displaying the pathology or symptomatology of the disease, condition or disorder (i.e., including arresting further development of the pathology and/or symptomatology); and (3) at least partially ameliorating the disease or condition; for example, ameliorating a disease, condition or disorder in an individual who is experiencing or displaying the pathology or symptomatology of the disease, condition or disorder (i.e., including reversing the pathology and/or symptomatology).

The inhibitor of HER2, HER3, or of the heterodimerization of HER2/HER3 may be provided in a composition that is formulated for any type of administration. For example, the compositions may be formulated for administration orally, topically, parenterally, enterally, or by inhalation. The inhibitor of HER2, HER3, or of the heterodimerization of HER2/HER3 may be formulated for neat administration, or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspending/dispersing agent, tablet-disintegrating agent, encapsulating material, film former or coating, flavoring agent, or printing ink. Any material used in preparing any dosage unit form is preferably pharmaceutically pure and substantially non-toxic in the amounts employed. In addition, the inhibitor of HER2, HER3, or of the heterodimerization of HER2/HER3 may be incorporated into sustained-release preparations and formulations. Administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the active ingredient is mixed with a carrier, diluent or excipient having the necessary compression properties in suitable proportions and compacted in the shape and size desired. For oral therapeutic administration, the active compound may be incorporated with the carrier, diluent, or excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained.

Liquid carriers, diluents, or excipients may be used in preparing solutions, suspensions, emulsions, syrups, elixirs, and the like. The active ingredient of this invention can be dissolved or suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents and excipients, for example, for oral, topical, or parenteral administration, include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating inhibitor of HER2, HER3, or of the heterodimerization of HER2/HER3 in the pharmaceutically appropriate amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and freeze drying techniques that yield a powder of the active ingredient or ingredients, plus any additional desired ingredient from the previously sterile-filtered solution thereof.

Thus, the inhibitor of HER2, HER3, or of the heterodimerization of HER2/HER3 may be administered in an effective amount by any of the conventional techniques well-established in the medical field. For example, the administration may be in the amount of about 0.1 mg/day to about 500 mg per day. In some embodiments, the administration may be in the amount of about 250 mg/kg/day. Thus, administration may be in the amount of about 0.1 mg/day, about 0.5 mg/day, about 1.0 mg/day, about 5 mg/day, about 10 mg/day, about 20 mg/day, about 50 mg/day, about 100 mg/day, about 200 mg/day, about 250 mg/day, about 300 mg/day, or about 500 mg/day.

In order to minimize the unwanted effects of the mechanically-induced lung injury or lung-stretch injury in the subject, the administration of the inhibitor of HER2, HER3, or of the heterodimerization of HER2/HER3 preferably occurs as soon as possible after detection of the injury. For example, administration preferably occurs within a minute, within five minutes, within 10 minutes, within 15 minutes, within 20 minutes, within 30 minutes, within 40 minutes, within 45 minutes, within 50 minutes, within 60 minutes, with 70 minutes, within 80 minutes, within 90 minutes, or within 2 hours of the injury is detected.

Figure 5A:
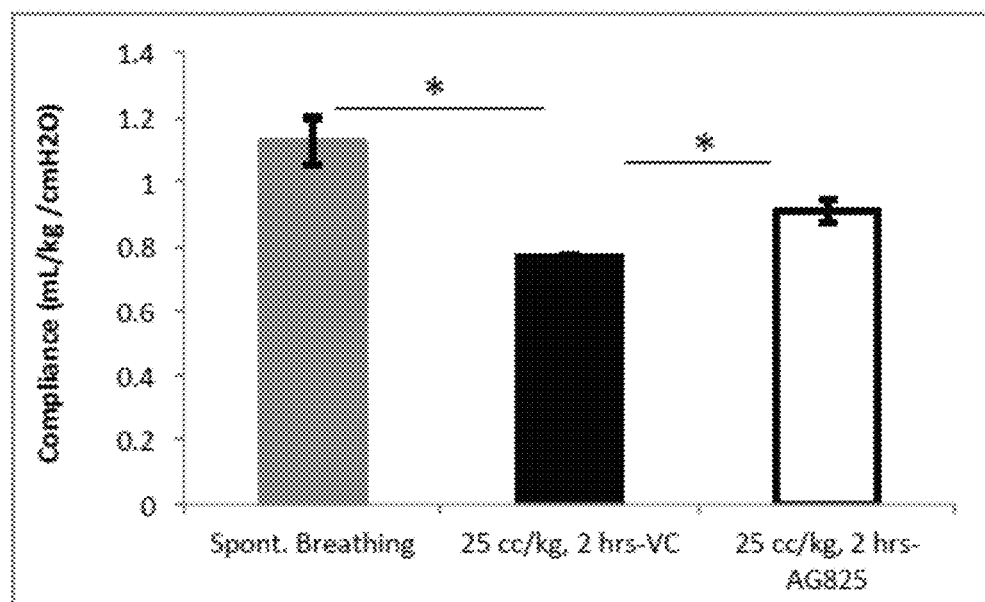
FIGS. 5A and 5B depict the present finding that HER2 inhibition preserves lung compliance (5A) and moderates permeability (5B) during large tidal volume mechanical ventilation.
Figure 5B:
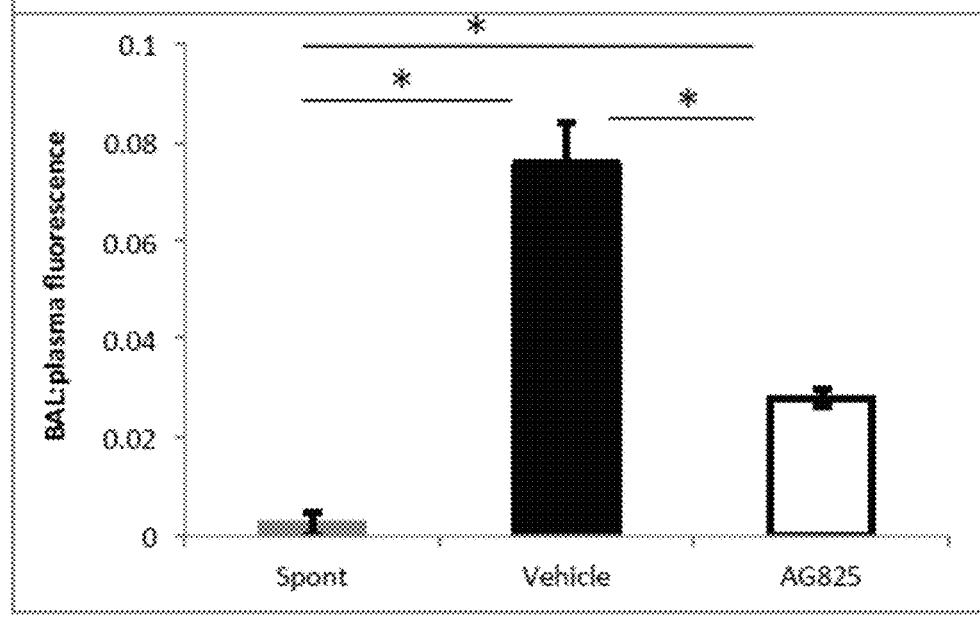

Also disclosed are methods for increasing lung compliance, moderating alveolar epithelial permeability, or both in a subject having a mechanically-induced lung injury or a lung-stretch injury comprising administering to the subject an inhibitor of human epidermal growth factor receptor 2 (HER2) or human epidermal growth factor receptor 3 (HER3), or an inhibitor of the heterodimerization of HER2/HER3, thereby increasing lung compliance, moderating alveolar epithelial permeability, or both in the subject. As shown in FIGS. 5A and 5B, administration of AG825 preserves lung compliance and preserves barrier properties/moderates unwanted permeability during large tidal volume mechanical ventilation. Thus, the present methods can be used to increase lung compliance and/or moderate alveolar epithelial permeability in a subject in need thereof as a result, for example, of ventilator induced injury or other cause of lung stretch. The characteristics of the recited inhibitors, the step of administering the inhibitors, and the other aspects of the present methods may be in accordance with the previously described methods for treating a mechanically-induced lung injury or lung stretch injury.

The present disclosure also pertains to methods for protecting a subject against a decrease in lung compliance, an increase in alveolar epithelial permeability, or both, as a result of a mechanically-induced lung injury or a lung-stretch injury comprising administering to the subject an inhibitor of human epidermal growth factor receptor 2

(HER2) or human epidermal growth factor receptor 3 (HER3), or an inhibitor of the heterodimerization of HER2/HER3, thereby protecting the subject against a decrease in lung compliance, an increase in alveolar epithelial permeability, or both. In accordance with the present methods, a subject may be protected against the negative effects of a mechanically-induced lung injury or a lung-stretch injury, including a decrease in lung compliance or an undesirable increase in alveolar epithelial permeability. Although a subject having sustained such injuries may have suffered either or both of the described negative effects, the present methods can be used to slow down the rate at which a decrease in lung compliance occurs or an undesirable increase in alveolar epithelial permeability occurs, to substantially halt the rate at which a decrease in lung compliance occurs or an undesirable increase in alveolar epithelial permeability occurs, or even to reverse such unwanted effects. The characteristics of the recited inhibitors, the step of administering the inhibitors, and the other aspects of the present methods may be in accordance with the previously described methods for treating a mechanically-induced lung injury or lung stretch injury.

Also provided are methods comprising administering an inhibitor of human epidermal growth factor receptor 2 (HER2) or human epidermal growth factor receptor 3 (HER3), or an inhibitor of the heterodimerization of HER2/HER3 to a subject that is undergoing or is to undergo mechanical ventilation. In accordance with such methods, the recited inhibitor may be administered to the subject regardless of whether or not a ventilation-induced lung injury has actually been detected. In this way, the subject can be protected against the effects of possible injury, for example, a decrease in lung compliance, an increase in alveolar epithelial permeability, or both. Subjects that are perceived to be at high risk for possible ventilation-induced lung injury, such as those already suffering from lung conditions, elderly patients, or young patient, can particularly benefit from the instant methods.

When the subject is already undergoing mechanical ventilation, the present methods can comprise administration of the inhibitor to a subject within a set period of time following initiation of the mechanical ventilation, for example, within 5 minutes, within 10 minutes, within 30 minutes, within 1 hour, within 2 hours, within 5 hours, within 10 hours, within 12 hours, within 18 hours, within 24 hours, within 2 days, within 3 days, within 4 days, or within 5 days following the initiation of mechanical ventilation.

When the subject is has not yet been subjected to mechanical ventilation, but will be subjected to mechanical ventilation, the present methods can comprise administration of the inhibitor to a subject within a set period of time prior to initiation of the mechanical ventilation, for example, within about 1 day, within about 18 hour, within about 12 hours, within about 10 hours, within about 8 hours, within about 6 hours, within about 4 hours, within about 2 hours, within about 1 hour, within about 45 minutes, within about 30 minutes, within about 20 minutes, within about 15 minutes, within about 10 minutes, or within about 5 minutes prior to the initiation of mechanical ventilation.

The characteristics of the recited inhibitors, the step of administering the inhibitors, and the other aspects of the present methods may be in accordance with the previously described methods for treating a mechanically-induced lung injury or lung stretch injury.

Supplemental information and data concerning the presently disclosed subject matter is included in U.S. Provisional Application No. 62/278,299, filed Jan. 13, 2016, including Appendix I.

Example 1—HER2, HER3 Inhibition Mitigates Stretch-Induced Barrier Properties

BACKGROUND

Although adherens junctions, desmosomes and gap junctions contribute to cell-cell adhesion and signaling in the alveolar epithelium, none of these cellular structures contributes significantly to passive paracellular barrier function. Instead, the gasket-like tight junctions (TJ) between adjacent Type I epithelial cells are the primary barrier to paracellular transport. Occludin and claudins (4, 5, 7 and 18) are the principal TJ proteins regulating paracellular barrier resistance and charge selectivity in the Type I lung epithelium, as well as zonula occludens (ZO-1, located between TJ proteins and cytoskeletal proteins). TJ permeability is correlated with actin-bound pools of TJ proteins, occluding ubiquitination, and quantities of total and phosphorylated TJ proteins, and actin rearrangement.

The presently described study focused on stretch-initiated HER2-HER3 mediated regulation of TJ protein composition and arrangement. Previously, HER signaling has been linked to epithelial TJ protein organization, with HER2 activation, and not EGFR activation, leading to loss of cell polarity and relocalization of TJ protein ZO-1. The HER3 ligand NRG1 has separately been implicated in increased barrier permeability in vivo: mice treated with bleomycin to induce lung injury had decreased alveolar protein content when treated with the ADAM17 sheddase inhibitor TAPI2 relative to untreated mice, thereby affirming the role of NRG1 and HER2 activation in the worsening of barrier function. The present investigators have shown that stretch alters tight junction protein expression, partially mediated by ERK. In addition, we have shown that stretched RAEC monolayer permeability is partially rescued by individual inhibitors for Rac1, ERK and PI3K. It is also well established that the actin cytoskeleton is regulated by Rac1 signaling; more specifically, Rac1 has been shown to be essential for growth-factor-induced signal transduction pathways that lead to organization of actin. It was presently hypothesized that HER2-HER3 activation is upstream of Rac1, ERK, and PI3K, conferring superior therapeutic potential for VILI.

In summary, because TJ protein composition mediates increased alveolar permeability, and HER, ERK and Rac1 signaling has been implicated in TJ assembly and actin reorganization, the present study represented an attempt to determine the specific role of HER2-HER3 activation in altering TJ proteins and worsening barrier function in vitro, and test the relevance of inhibiting HER2 as a potential injury intervention in our in vivo rodent model of VILI.

Presented herein is data demonstrating that 1) cyclic stretch increases RAEC monolayer permeability; and that 2) inhibition of NRG1 expression, release, NRG1 binding to HER3, and HER2 activation each attenuates stretch-associated permeability increases, to a degree comparable to direct inhibition of Rac1 and PI3K inhibition and ERK. Furthermore, it is shown herein that lung slices and RAECs have similar levels of stretch-induced TJ protein dissociation. Finally, provided is exciting and unexpected proof-of-principle data demonstrating that HER2 inhibition mediates TJ protein rearrangement in stretched lung cells and slices in vitro and maintains barrier properties during prolonged mechanical ventilation with moderate tidal volumes in vivo.

The following data demonstrates the present finding that HER2-HER3 mediates RAEC monolayer permeability. As evidence that NRG1, HER2, and HER3 regulate stretch-associated increases in permeability, RAEC monolayers (N≥3-7/group) were exposed to 10 min of stretch, and compared vehicle controls (VC, black bars, FIG. 16—Appendix I) with those pretreated microRNA miR15-b to reduce NRG1 expression (FIG. 7, APPROACH—Appendix I), TAPI2 to inhibit ADAM17 and NRG1 cleavage (diagonal striped bars, FIG. 16—Appendix I), HER3 mAb to inhibit NRG1 binding (dark gray bars), or AG825 (white bars) to inhibit HER2 activation. All treatments significantly reduced stretch-associated permeability at least as effectively as inhibiting ERK and PI3K directly (horizontal stripe U0126, dotted bars EHT-1864), such that AG825 and HER3 neutralizing Ab HER2-HER3 blockade maintained barrier properties at unstretched levels (no significance vs. unstretched VC). The superior barrier protection offered by inhibiting HER2-HER3 activation over inhibiting sheddase ADAM17 establishes that any direct role of other pathways on the purported upstream regulators of permeability (e.g., ROS release, EGFR transactivation) is small. These studies demonstrate that stretch-induced paracellular permeability increases are predominantly mediated by HER2-HER3 signaling pathways.

In the extracellular domain, the TJ is composed of claudins and occludin bound to TJ proteins of neighboring cells. In the intracellular domain, the claudins and occludin bind to actin via ZO-1. It was previously demonstrated that TJ protein content and arrangement is altered when stretch increases paracellular permeability, and a significant regulation of claudin-4 after VILI and its role in mediating lung permeability. The present study tests the hypothesis that TJ dissociation between the ZO1 and the claudins and occludin is the primary causal mechanism for HER2-HER3 mediated barrier disruption. As preliminary evidence, RAEC monolayers (N=4) that were pretreated with NRG1 cleavage inhibitor TAPI-2, HER2 inhibitor AG825, or vehicle (VC) were stretched. Using co-IP with ZO-1 as bait, a significant decrease (black bars, FIG. 17—Appendix I) was observed in claudin-4 and -7 bound to ZO-1 after just 10 min of cyclic stretch (with similar trends in occludin and claudin-18), compared to unstretched controls. The present study also confirmed stretch-induced TJ protein dissociation in lung slices. In RAECs, TJ dissociation with stretch was prevented by inhibition of NRG1 release (TAPI-2, diagonal bars) or HER2 activation (white bars), such that the levels of TJ bound to ZO-1 were equal or greater after stretch than unstretched controls. Thus, it was demonstrated herein that TJ protein dissociation during stretch is mediated by NRG1-mediated HER2 signaling.

To determine the causal relationships between stretch-initiated HER2 activation and the alternation of TJ protein expression and arrangement, RAEC and PCLS from independent isolations were subjected to cyclic stretch for 10 min and 60 min (N=7 rats for each outcome measure, at each timepoint), at 0, 25, 37% ASA. To assess the effects of a longer stretch duration, RAEC monolayers from additional isolations (n=7 rats) were also subjected to cyclic stretch ASA of 0% (control) or 25% for 6 hrs. For every isolation, functional relationships will be confirmed in unstretched and stretched control groups treated with AG825 (HER2 inhibitor), anti-HER3ab (HER3 inhibitor), and tempol or tiron (superoxide scavenger), and compared with unstretched RAEC and PCLS treated with PMA to activate HER3 via NRG1 shedding as a positive control. In RAECs, results were compared to stretched and unstretched monolayers with separate treatments to evaluate downstream signaling pathway inhibition of ERK (U0126), PI3K (Wortmannin), Rac1 (EHT-1864 and ERK 1/2 siRNA [97] and LIMK1 (BMS4). Additional groups had NRG1 expression decreased by overexpressing miRNA-15b (negative regulator of NRG1), using scrambled oligonucleotide as a negative control. As a validation of or hierarchical platform, TJ expression, phosphorylation and arrangement results in PCLS were compared with RAECs. In all groups, monolayers were assigned to one of four quantitative outcome evaluations: alveolar paracellular permeability via BODIPY-oubain and streptavidin-FITC methods (see INNOVATION—Appendix I), TJ and actin arrangement by fixing RAECs and PCLSs for qualitative immunofluorescence, total and phosphorylated TJ content via Western blot, or ZO-1-bound TJ proteins by isolating protein for co-IP using ZO-1 as bait, followed by Western blotting for occludin, claudins 4, 7, and 18, and F-actin in the ZO-1 protein fraction.

In vivo validation: the present data (N=3 rats/group, Vt=25 ml/kg for 4 hrs, PEEP=0, rate 27 bpm, FiO2=0.21) demonstrate VILI in vivo, with associated with increased permeability and decreased lung compliance (black bars, FIG. 18—Appendix I), compared to spontaneously breathing rats (orange bars). HER2 inhibition dramatically protects against VILI (AG825 1.67 mg/kg/day IP, 3 days), with significant improvements in lung compliance and permeability (white bars). To translate in vitro findings to demonstrate the role of HER2-HER3 to modulate barrier properties in vivo in animals ventilated at large tidal volumes, anesthetized, intubated Sprague-Dawley male rats (N=7/group, 250-300 grams) were assigned to receive mechanical ventilation for 4 hrs at 25 mL/kg tidal volume ventilation with 0 positive end-expiratory pressure, or served as spontaneously breathing controls. Ventilated rats received one of 2 treatments, intratracheal TAPI2 (used in vivo to inhibit NRG1 sheddase ADAM17) or intraparenteral AG825 or intravenous trastuzumab (to inhibit HER2), or will serve as ventilated vehicle-treated controls. Treatment windows were varied from 3 days prior ventilation to concurrent application, to identify an optimal, clinically-relevant therapeutic dose and timing. Dynamic compliance will be measured every 30 min. All animals were injected with FITC-albumin prior to ventilation, and alveolar permeability assessed prior to sacrifice by quantifying fluorescence of bronchoalveolar lavage (BAL) fluid normalized to serum fluorescence. Lungs were formalin-fixed after BAL, and hematoxylin/eosin stained sections were evaluated for hyaline membrane formation, interstitial edema, margination and infiltration of neutrophils, as well as intra-alveolar and perivascular hemorrhage. Compliance, permeability, and lung histology were compared across groups.

What is claimed:

1. A method for treating a mechanically-induced lung injury or a lung-stretch injury comprising
    identifying a subject having a mechanically-induced lung injury or a lung-stretch injury, and
    administering to the subject an inhibitor of human epidermal growth factor receptor 2 (HER2) or human epidermal growth factor receptor 3 (HER3), or an inhibitor of the heterodimerization of HER2/HER3.

2. The method according to claim 1 comprising administering to the subject an inhibitor of HER2.

3. The method according to claim 1 comprising administering to the subject an inhibitor of HER3.

4. The method according to claim 1 comprising administering to the subject an inhibitor of the heterodimerization of HER2/HER3.

5. The method according to claim 1, wherein the subject has a mechanically-induced lung injury.

6. The method according to claim 5, wherein the subject has a ventilator-induced lung injury.

7. The method according to claim 1, wherein the subject has a lung-stretch injury.

\* \* \* \* \*